United States Patent
Wright et al.

(10) Patent No.: US 6,697,153 B1
(45) Date of Patent: *Feb. 24, 2004

(54) METHOD AND APPARATUS FOR ANALYZING LINE STRUCTURES

(75) Inventors: Marilyn I. Wright, Austin, TX (US); James B. Stirton, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 31 days.

This patent is subject to a terminal disclaimer.

(21) Appl. No.: 10/079,358

(22) Filed: Feb. 20, 2002

(51) Int. Cl.[7] .............................................. G01N 21/88
(52) U.S. Cl. .................................. 356/237.4; 356/237.5
(58) Field of Search ................ 356/237.1, 237.2–237.6, 356/392, 394, 601–613, 636, 239.7, 239.8

(56) References Cited

U.S. PATENT DOCUMENTS

| | | | |
|---|---|---|---|
| 6,051,348 A | 4/2000 | Marinaro et al. ............. 430/30 |
| 6,245,584 B1 | 6/2001 | Marinaro et al. ............. 438/14 |
| 6,429,943 B1 * | 8/2002 | Opsal et al. ................. 356/625 |
| 6,433,878 B1 * | 8/2002 | Niu et al. .................... 356/603 |
| 6,538,731 B2 * | 3/2003 | Niu et al. ................. 356/237.5 |

* cited by examiner

*Primary Examiner*—Richard A. Rosenberger
*Assistant Examiner*—Vincent P. Barth
(74) *Attorney, Agent, or Firm*—Williams, Morgan & Amerson, P.C.

(57) ABSTRACT

A method and an apparatus for analyzing line structures during semiconductor wafer processing. At least one semiconductor wafer is processed. Metrology data from the processed semiconductor wafer is acquired. Film property data from the semiconductor wafer is acquired. Data from a reference library is accessed; the data comprising optical data relating to a line structure formation on a semiconductor wafer, based upon the film property data. The metrology data is compared to data from the reference library. A line structure fault detection analysis is performed in response to the comparison of the metrology data and the reference library data.

34 Claims, 11 Drawing Sheets

METHOD AND APPARATUS FOR ANALYZING LINE STRUCTURES

BACKGROUND OF THE INVENTION

1. Field of the Invention

This invention relates generally to semiconductor manufacturing, and, more particularly, to a method and apparatus for detecting reduced line width(s) over a field/active transition region.

2. Description of the Related Art

The technology explosion in the manufacturing industry has resulted in many new and innovative manufacturing processes. Today's manufacturing processes, particularly semiconductor manufacturing processes, call for a large number of important steps. These process steps are usually vital, and therefore, require a number of inputs that are generally fine-tuned to maintain proper manufacturing control.

The manufacture of semiconductor devices requires a number of discrete process steps to create a packaged semiconductor device from raw semiconductor material. The various processes, from the initial growth of the semiconductor material, the slicing of the semiconductor crystal into individual semiconductor wafers, the fabrication stages (etching, doping, ion implanting, or the like), to the packaging and final testing of the completed device, are so different from one another and specialized that the processes may be performed in different manufacturing locations that contain different control schemes.

Generally, a set of processing steps is performed on a group of semiconductor wafers, sometimes referred to as a lot, using a semiconductor manufacturing tool called an exposure tool or a stepper. Typically, an etch process is then performed on the semiconductor wafers to shape objects on the semiconductor wafer, such as line structures (e.g., polysilicon lines), each of which may function as a gate electrode for a transistor. As another example, a plurality of metal lines, e.g., aluminum, may be formed that serve as conductive lines that connect one conductive region on the semiconductor wafer to another. The manufacturing tools communicate with a manufacturing framework or a network of processing modules. Each manufacturing tool is generally connected to an equipment interface. The equipment interface is connected to a machine interface to which a manufacturing network is connected, thereby facilitating communications between the manufacturing tool and the manufacturing framework. The machine interface can generally be part of an advanced process control (APC) system. The APC system initiates a control script, which can be a software program that automatically retrieves the data needed to execute a manufacturing process.

FIG. 1 illustrates a typical semiconductor wafer 105. The semiconductor wafer 105 typically includes a plurality of individual semiconductor die arranged in a grid 150. Photolithography steps are typically performed by a stepper on approximately one to four die locations at a time, depending on the specific photomask employed. Photolithography steps are generally performed to form patterned layers of photoresist above one or more process layers that are to be patterned. The patterned photoresist layer can be used as a mask during etching processes, wet or dry, performed on the underlying layer or layers of material, e.g., a layer of polysilicon, metal or insulating material, to transfer the desired pattern to the underlying layer. The patterned layer of photoresist is comprised of a plurality of features, e.g., line-type features, such as a polysilicon line, or opening-type features, that are to be replicated in an underlying process layer.

Turning now to FIG. 2A, a diagram depicting a top view of a portion of a semiconductor wafer comprising a plurality of line structures 155, is illustrated. In one embodiment, the line structures 155 are formed across a field region 120 and an active region 130. FIG. 2B illustrates a side view diagram of a line structure 155 formed across a field region 120 and an active region 130. In one embodiment, the field region 120 and the active region 130 are formed on a surface 160 of a silicon substrate 170. In one embodiment, the line structures 155 are formed above the field region 120 and the active region 130. One example of the line structure 155 is a poly-silicon line. In one embodiment, the line structure 155 provides an electrical line connection from a gate of a transistor (not shown) to another portion of the transistor.

The line structures 155, such as polysilicon lines and the like, can contain various errors. One such line structure error is a line edge error, where an excessive amount of roughness exists on the line edges. Errors on line structures can cause current leakage problems, thereby reducing the efficiency of the operation of transistors formed on the semiconductor wafer 105. Furthermore, line structure errors can result in excessive variations in the operation speed of circuits formed on the semiconductor wafer 105, such as transistors.

Errors in the line structures 155 can cause quality degradation of the semiconductor wafer 105 being processed. Tests that are used for detecting errors in the line structures 155 can be inefficient and/or destructive in nature, and can be very. time consuming. Often, the tests that are used to detect errors in the line structures 155 can cause interruptions in the production line during semiconductor manufacturing processes.

The present invention is directed to overcoming, or at least reducing the effects of, one or more of the problems set forth above.

SUMMARY OF THE INVENTION

In one aspect of the present invention, a method is provided for analyzing line structures during semiconductor wafer processing. At least one semiconductor wafer 105 is processed. Metrology data from the processed semiconductor wafer 105 is acquired. Film property data from the semiconductor wafer 105 is acquired. Data from a reference library is accessed; the data comprising optical data relating to a line structure formation on a semiconductor wafer 105, based upon the film property data. The metrology data is compared to data from the reference library. A line structure fault detection analysis is performed in response to the comparison of the metrology data and the reference library data.

In another aspect of the present invention, a system is provided for analyzing line structures during semiconductor wafer 105 processing. The system of the present invention comprises: a computer system; a manufacturing model coupled with the computer system, the manufacturing model being capable of generating and modifying at least one control input parameter signal; a machine interface coupled with the manufacturing model, the machine interface being capable of receiving process recipes from the manufacturing model; a processing tool capable of processing semiconductor wafers 105 and coupled with the machine interface, the first processing tool being capable of receiving at least one control input parameter signal from the machine interface; a metrology tool coupled with the first processing tool and the second processing tool, the metrology tool being capable of acquiring metrology data; an optical data reference library, the optical data reference library comprising optical data related to a plurality of line structures 155; and an optical data error analysis unit coupled to the metrology tool and the optical data reference library, the scatterometry data error analysis unit capable of comparing the metrology data to corresponding data in the optical data reference library and calculating at least one of a line-edge error and a line structure in response to the comparison.

BRIEF DESCRIPTION OF THE DRAWINGS

The invention may be understood by reference to the following description taken in conjunction with the accompanying drawings, in which like reference numerals identify like elements, and in which.

Figure 1:
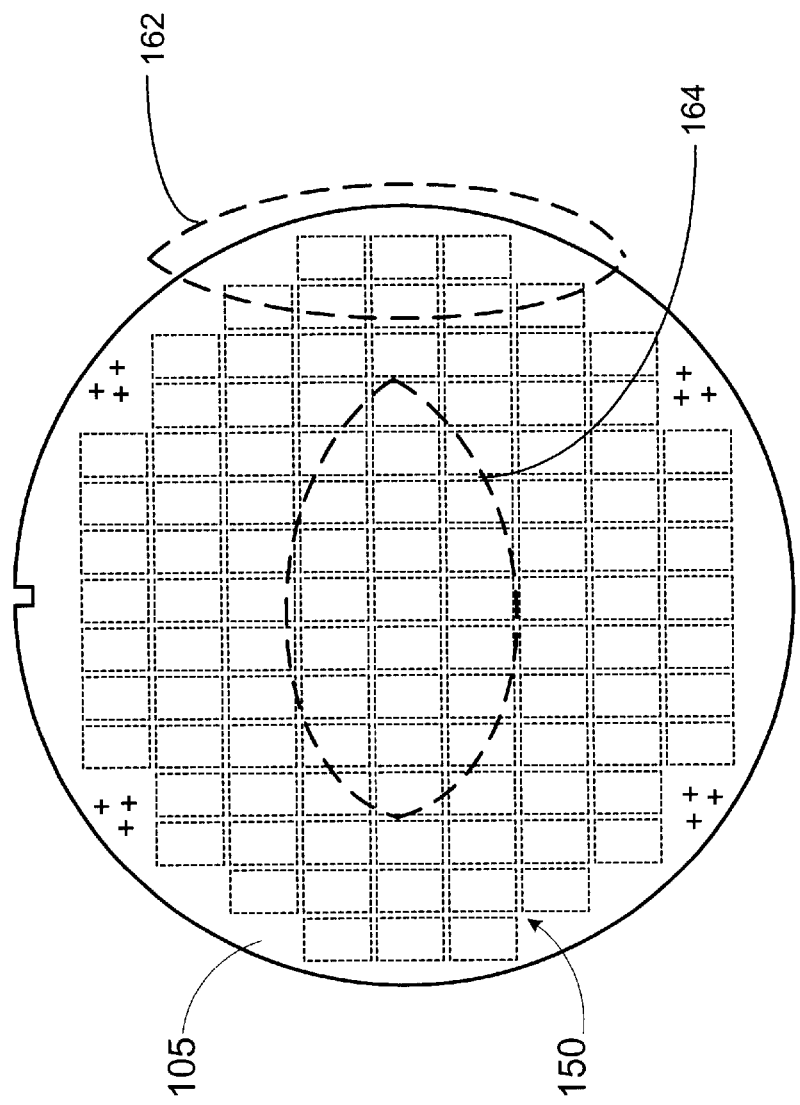
FIG. 1A is a simplified diagram of a prior art semiconductor wafer being processed.
Figure 2A:
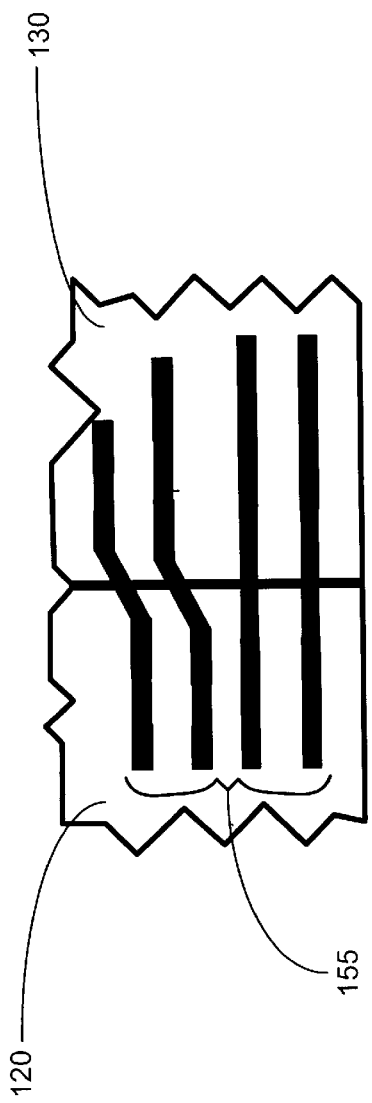
FIG. 2A is a top view of a line structure placed on an area on a semiconductor wafer that transitions from a field region to an active region.
Figure 2B:
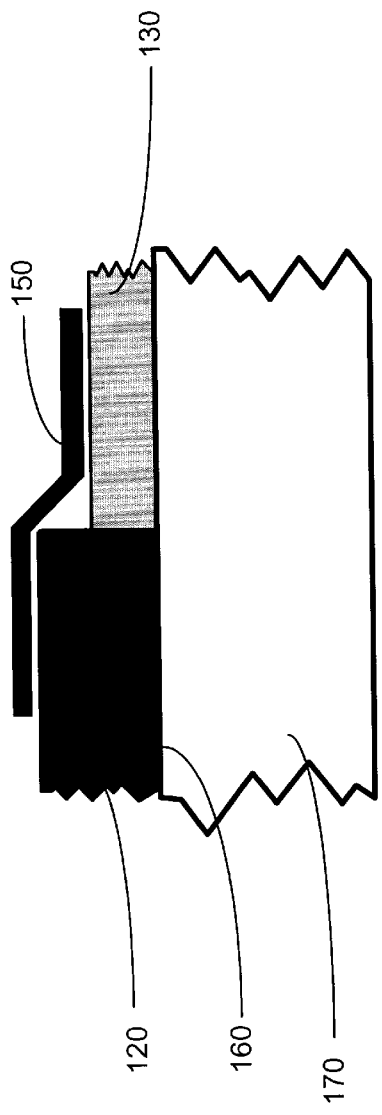
FIG. 2B is a cross-sectional view of a line structure placed on an area on a semiconductor wafer that transitions from a field region to an active region.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discreet processes that are involved in semiconductor manufacturing. Many times, semiconductor devices are stepped through multiple manufacturing process tools. Errors that can occur during the formation of the line structures 155, such as polysilicon lines, on semiconductor wafers 105 being processed can cause significant degradation of the semiconductor wafers 105 being manufactured. Embodiments of the present invention utilize an optical data acquisition tool, such as a scatterometer, ellipsometer, and the like, to detect and/or to reduce errors relating to the line structures 155, such as excessive line-edge roughness, formed on the semiconductor wafers 105.

Figure 3:
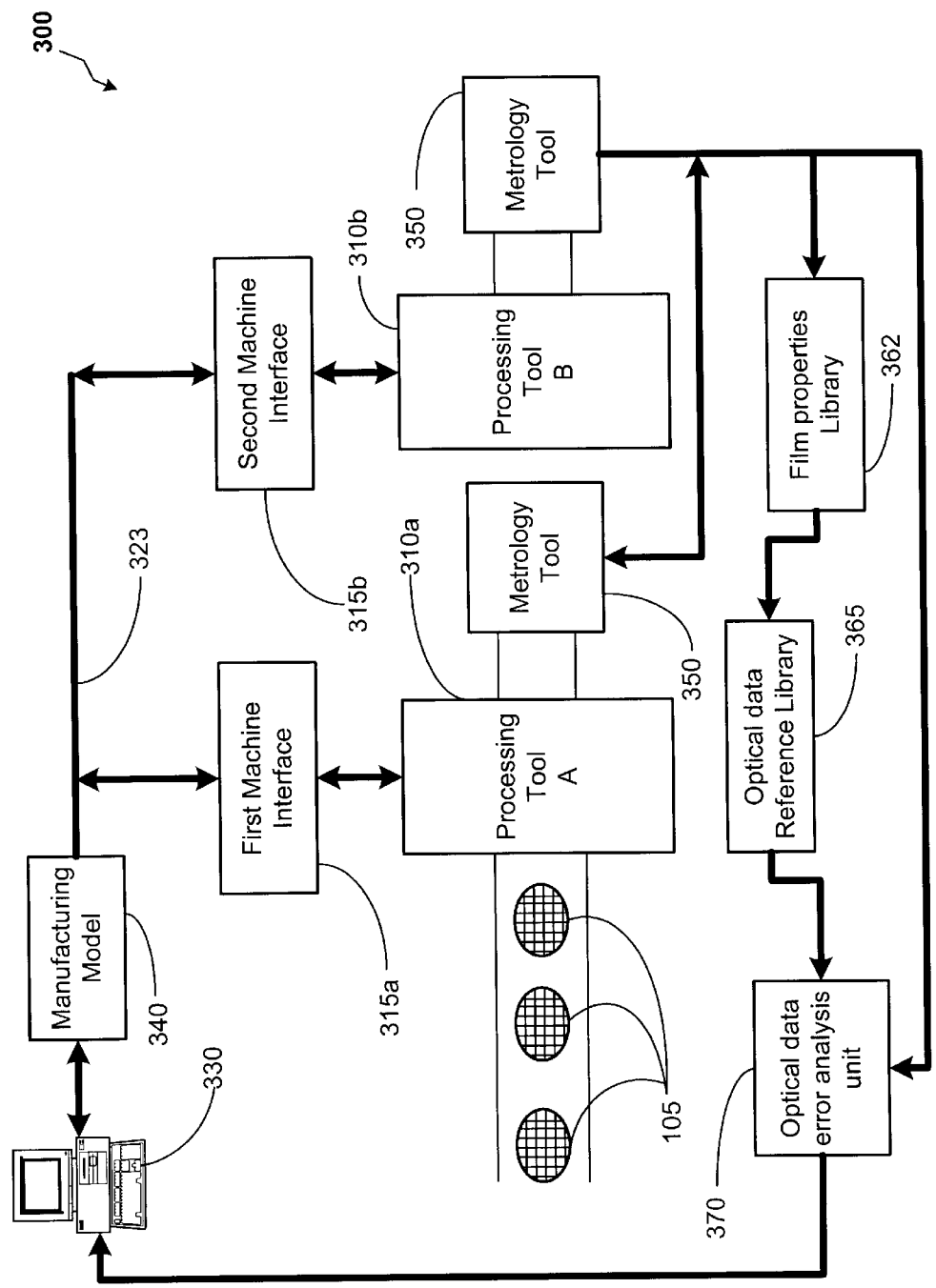
FIG. 3 is a block diagram representation of a system in accordance with one embodiment of the present invention.

Semiconductor devices are processed in a manufacturing environment using a number of input control parameters. Turning now to FIG. 3, a system 300 in accordance with one embodiment of the present invention is illustrated. In one embodiment, semiconductor wafers 105, are processed on processing tools 310a, 310b using a plurality of control input signals, or manufacturing parameters, on a line 323. In one embodiment, control input signals, or manufacturing parameters, on the line 323 are sent to the processing tools 310a, 310b from a computer system 330 via machine interfaces 315a, 315b. In one embodiment, the first and second machine interfaces 315a, 315b are located outside the processing tools 310a, 310b. In an alternative embodiment, the first and second machine interfaces 315a, 315b are located within the processing tools 310a, 310b.

In one embodiment, the computer system 330 sends control input signals, or manufacturing parameters, on the line 323 to the first and second machine interfaces 315a, 315b. The computer system 330 employs a manufacturing model 340 to generate the control input signals on the line 323. In one embodiment, the manufacturing model 340 contains a manufacturing recipe that determines a plurality of control input parameters that are sent on the line 323.

In one embodiment, the manufacturing model 340 defines a process script and input control that implement a particular manufacturing process. The control input signals on the line 323 that are intended for processing tool A 310a are received and processed by the first machine interface 315a. The control input signals on the line 323 that are intended for processing tool B 310b are received and processed by the second machine interface 315b. Examples of the processing tools 310 used in semiconductor manufacturing processes are steppers, step-and-scan tools, etch process tools, and the like.

One or more of the semiconductor wafers 105 that are processed by the processing tools 310a, 310b can also be sent to a metrology tool 350 for acquisition of metrology data. The metrology tool 350 can be a scatterometry data acquisition tool, an overlay-error measurement tool, a critical dimension measurement tool, and the like. In one embodiment, the metrology tool 350 examines one or more processed semiconductor wafers 105.

The system 300 comprises a film properties library 362 and an optical data reference library 365. In one embodiment, the optical data reference library 365 comprises data relating to calculated optical data of a plurality of structures on a semiconductor wafer 105. In an alternative embodiment, the optical data reference library 365 comprises data relating to reflected optical data that occurs in response to optical stimuli engaged upon particular structures on a semiconductor wafer 105. A record that contains the response to optical stimuli performed on a plurality of structures can be organized and stored in the optical data reference library 365, and used as reference for comparison of actual semiconductor wafer data during manufacturing processes.

The system 300 uses the film properties library 362 and the optical data reference library 365 to more accurately find line structure variations or errors. Certain information regarding the grating structure, such as film thickness, critical dimensions, profile data, and the like, which are organized and stored in the film properties library 362, can be used to narrow down specific optical data in the optical data reference library 365. In one embodiment, the film properties library 362 may comprise optical data and other data relating to film thicknesses, critical dimensions measurements, profile data, and the like.

Acquired metrology data can be used to look up process data such a film thicknesses, critical dimensions, profile information, and the like, in the film properties library 362. The data from the film properties library 362 can then be used to fit resultant spectra from acquired optical metrology data into the optical data reference library 365 more accurately. In other words, when optical data is compared with optical reference data in the optical data reference library 365, the variations can be primarily attributed to line structure variations instead of factors such as film thicknesses, CD, profile information, and the like. Therefore, film properties variations can be assumed to be small and deviations from ideal modeling generally can be attributed to variations in the line structure characteristics, such as line-edge roughness and other line structure qualities. This provides for more efficient and accurate assessment of line structure characteristics.

The particular reflection profile expected for any structure on a semiconductor wafer 105 depends on the specific geometry of the structure and the parameters of the measurement technique employed by the metrology tool 350, such as a scatterometry tool. The reflection profile for a particular structure includes the bandwidth of the reflected light, the angle of incidence, and the like. The profiles in the optical data reference library 365 are typically calculated theoretically by employing Maxwell's equations based on the characteristics of the structures on the semiconductor wafer 105. The process for generating reference reflection profiles is well known to those of ordinary skill in the art, and accordingly, it is not described in greater detail herein for clarity and so as not to obscure the invention. It is also contemplated that profiles in the optical data reference library 365 may be confirmed empirically by measuring reflection profiles of sample semiconductor wafers 105 and subsequent characterization of the measured semiconductor wafers 105 by destructive or non-destructive examination techniques.

An optical data error analysis unit 370 is capable of comparing the metrology data from the metrology tool 350 and the libraries 362, 365 and determining if a significant error exists on the structure being analyzed. In one embodiment, the optical data error analysis unit 370 is a software unit that resides within the computer system 330. In an alternative embodiment, the optical data error analysis unit 370 is a hardware unit that is integrated into the system 300. In yet another embodiment, the optical data error analysis unit 370 is a firmware unit integrated within the system 300. The optical data error analysis unit 370 can be used by the system 300 to perform fault analysis of the semiconductor wafers 105 being manufactured, which is described in greater detail below. The optical data error analysis unit 370 can also be used by the system 300 to perform feedback process control, which is described in greater detail below.

Scatterometry metrology is a non-contact inspection technique used to acquire metrology data from the semiconductor wafer 105. Scatterometry measurements can be used for particle detection, estimation of particle sizing, and for roughness measurement of smooth silicon wafer surfaces. Scatterometry measurements are also useful for determining chemical-mechanical polishing (CMP) roughness, and provides for characterizing several film parameters.

Figure 4A:
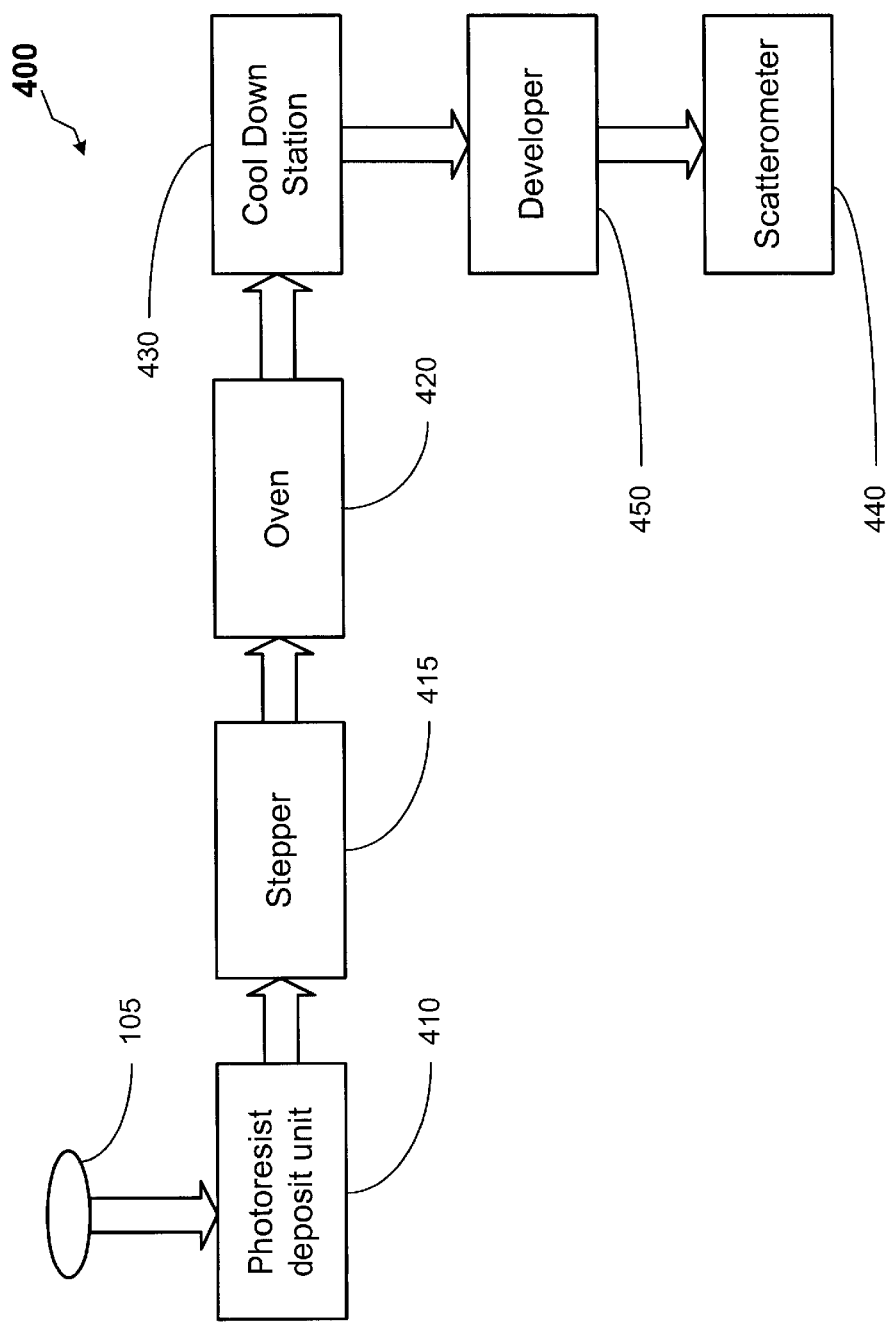
FIG. 4A illustrates one embodiment of a process flow in accordance with one embodiment of the present invention.

One embodiment of an implementation of a scatterometry metrology sequence in the context of semiconductor wafer 105 manufacturing, is shown in FIG. 4A, wherein an illustrative processing line 400 for performing photolithography patterning is depicted. The processing line 400 includes a photoresist deposition unit 410, a stepper 415, an oven 420, a cool down station 430, a developer 450, and a scatterometer 440. The photoresist deposition unit 410 receives a semiconductor wafer 105, and forms a layer of photoresist of a predetermined thickness above a process layer formed above the surface of the semiconductor wafer 105. The stepper 415 then receives the semiconductor wafer 105 and exposes the photoresist to a light source using a reticle to pattern the layer of photoresist. The semiconductor wafer 105 is transferred to the oven 420, where a post exposure bake process is conducted. Following the post exposure bake process, the semiconductor wafer 105 is transferred to the cool down station 430, and then to the developer station 450 after the semiconductor wafer 105 has sufficiently cooled. The soluble photoresist material is removed from the semiconductor wafer 105 in the developer station 450, thereby resulting in a patterned layer of photoresist.

The semiconductor wafer 105 is then transferred to the scatterometer 440 for measurements. As described in greater detail below, the scatterometer 440 measures the wafer 105 to determine the acceptability and/or uniformity of the previously performed photolithography processes. The computer system 330, which is integrated with the APC framework, based on the semiconductor wafer 105 measurements, can adjust the recipe of the stepper 415, as needed. As will be recognized by those of ordinary skill in the art in light of this disclosure, the processing line 400 may include discrete or integrated processing tools 310 for performing the processing steps described herein. The data acquired by the scatterometer 440 is used for making modifications to the control input signals on the line 323, which control the processing tools 310.

Figure 4B:
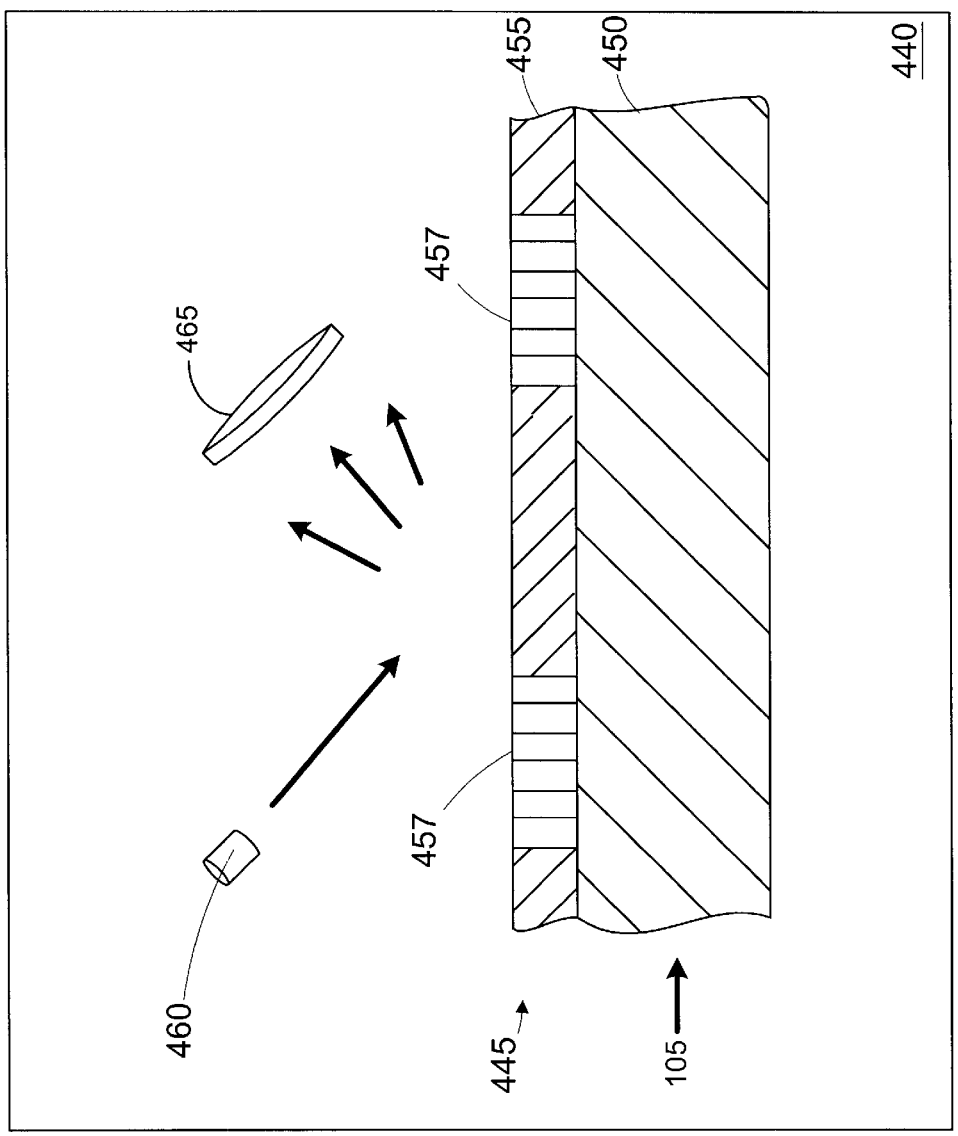
FIG. 4B illustrates a simplified view of a scatterometer with the semiconductor wafer loaded therein, in accordance with one embodiment of the present invention.

Referring to FIG. 4B, a simplified view of an illustrative scatterometer 440 with the semiconductor wafer 105 loaded therein is provided. The semiconductor wafer 105 has a base material 450. The photoresist layer 455 has regions 457 formed on the base material 450 resulting from the previous exposure and baking steps (i.e., referred to as a patterned photoresist layer 455). The chemical change resulting in the change in solubility of the regions 457 also results in the regions 457 having an index of refraction different than that of the unexposed portions of the photoresist layer 455.

In one embodiment, the scatterometer 440 comprises a light source 460 and a detector 465 positioned proximate the semiconductor wafer 105. The light source 460 of the scatterometer 440 illuminates at least a portion of the semiconductor wafer 105, and the detector 465 takes optical measurements, such as intensity, of the reflected light. Although the invention is described using a scatterometer 440 designed to measure reflected light intensity, it is contemplated that other measurement tools, such as an ellipsometer, a reflectometer, a spectrometer, or some other light-measuring device may be used. It is also contemplated that the scatterometer 440 may use monochromatic light, white light, or some other wavelength or combinations of wavelengths, depending on the specific implementation. The angle of incidence of the light may also vary, depending on the specific implementation.

The differences in the refractive indices for the regions 457 and the unexposed portions of the photoresist layer 455 cause light scattering, resulting in a decrease in the intensity of the reflected light, as compared to scattering in the photoresist layer 455 before exposure and/or baking. The scatterometer 440 measures the intensity at different points on the semiconductor wafer 105, such as on the periphery and in the middle. A difference in the light intensity between various points indicates a nonconformity, such as a variation in the line widths of the regions 457. The light analyzed by the scatterometer 440 typically includes a reflected component and a scattered component. The reflected component corresponds to the light component where the incident angle equals the reflected angle. The scattered component corresponds to the light component where the incident angle does not equal the reflected angle. For purposes of discussion hereinafter, the term "reflected" light is meant to encompass either or both the reflected component and the scattered component.

The computer system 330, in conjunction with the manufacturing model 340, adjusts the recipe of the stepper 415 to correct the nonconformity. For example, if the intensity measurement on the periphery 162 of the semiconductor wafer 105 (see FIG. 1) is greater than the intensity measurement in the middle 164, the line width is presumably less, because a smaller line width causes less scattering. To correct the line width variation, the computer system 330 changes the recipe of the stepper 415 such that the exposure sites (e.g., individual die or groups of die) with smaller line widths receive either an increased energy exposure or a longer duration exposure.

In an alternative embodiment, scatterometry measurements can be made before performing the develop process. Detecting variations and adjusting the stepper 415 recipe prior to performing the develop process allows for a quicker corrective action response. It is contemplated that all of the semiconductor wafers 105 in a lot may be tested, or only selected semiconductor wafers 105 in the lot. Identifying variations early allows correction of semiconductor wafers 105 within the same lot. For more stable steppers 415, the scatterometer 440 may be used only once per shift or once per week, depending on the specific implementation.

In the illustrated embodiment, the photoresist layer 455 is of a chemically-amplified type. In cases where a non-chemically-amplified photoresist material is used, the scatterometer 440 may be stationed prior to the oven 420. In a non-amplified photoresist system, the pattern is essentially complete after exposure in the stepper 415. The post exposure bake in the oven 420, which may be optional, is conducted to smooth the edges in the pattern resulting from standing waves, rather than to complete the patterning. Thus, the exposed portions already have an index of refraction different than the unexposed patterns, and the scatterometer 440 may be used. Scatterometry data is processed and correlated by the system 300. The scatterometry data is then analyzed by the optical data error analysis unit 370.

Figure 5:
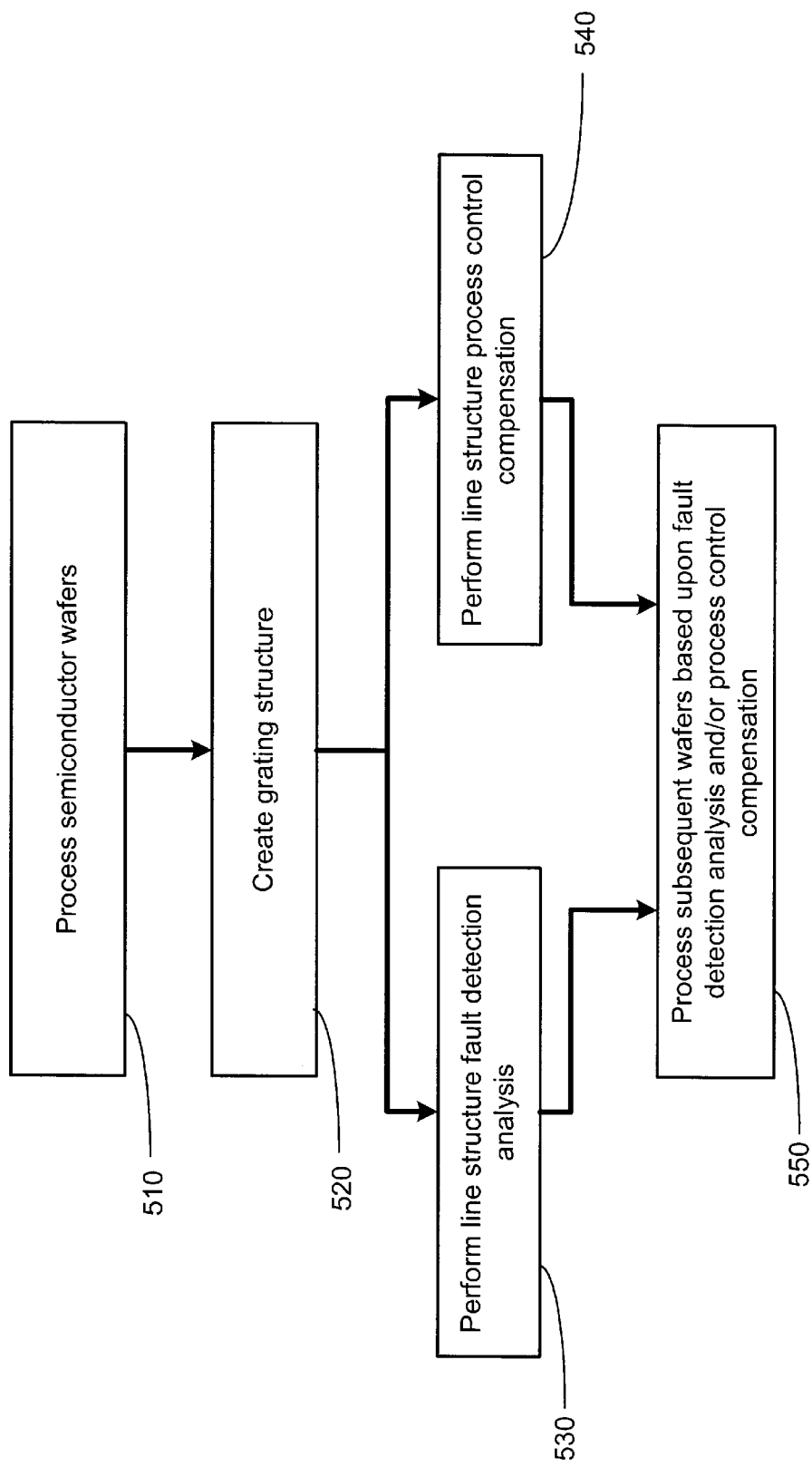
FIG. 5 illustrates a flowchart depiction of a method in accordance with one embodiment of the present invention.
Figure 6:
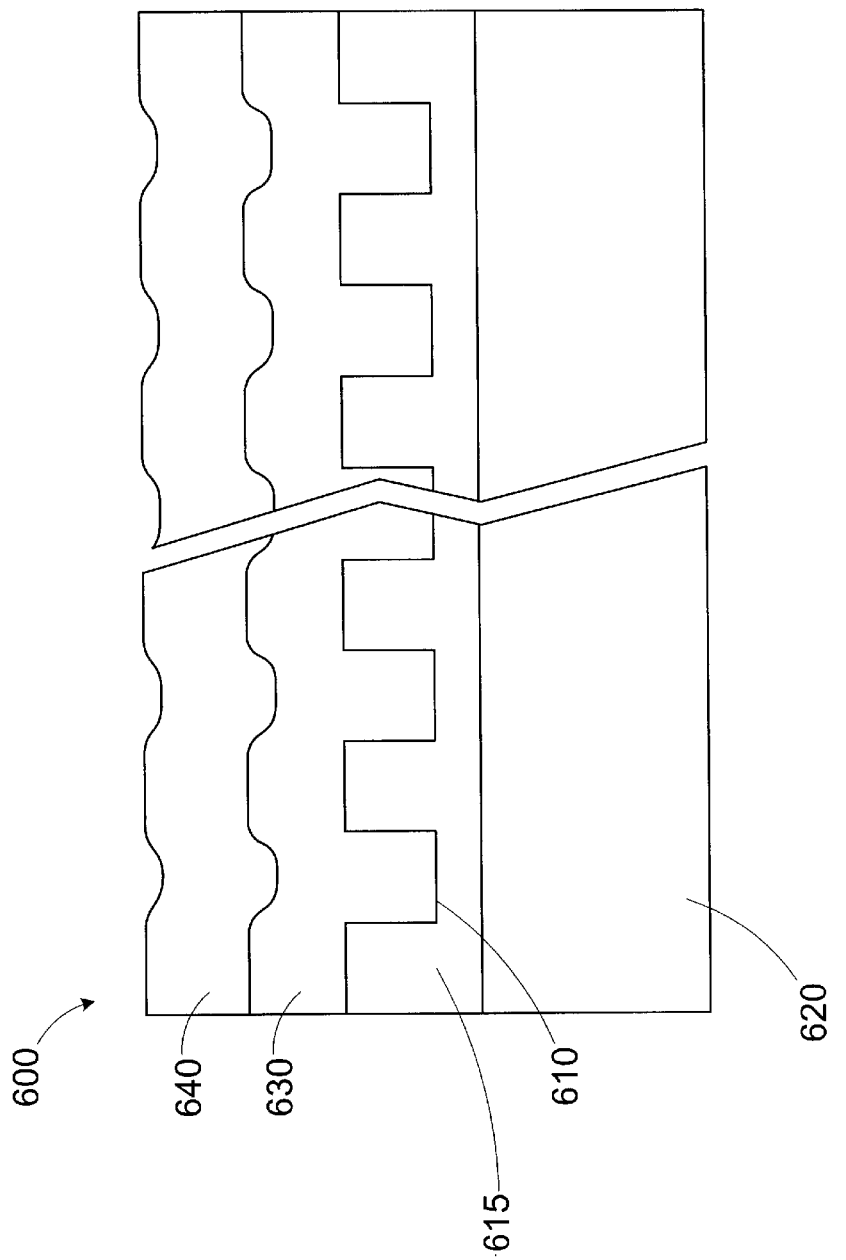
FIG. 6 is a cross sectional view of a grating structure after the formation of a silicon nitride stop layer and a silicon dioxide layer used to form grating features on the semiconductor wafer of FIG. 1, in accordance with one embodiment of the present invention.

Turning now to FIG. 5, a flowchart depiction of one embodiment of a method in accordance with the present invention, is illustrated. Semiconductor wafers 105, or a manufacturing-lot of semiconductor wafers 150, are processed (block 510). In one embodiment, a photolithography process followed by an etching process is performed. During the processing of the semiconductor wafers 105, a grating structure is formed on the semiconductor wafer 105 being processed (block 520). In one embodiment, the grating structure is formed on the thickest photoresist layer on the semiconductor wafer 105. Alternatively, a grating structure can be formed above a silicon substrate. FIG. 6 illustrates a grating structure 600 that is formed in a process layer 615 that is formed above a silicon substrate 620.

In one embodiment, a grating structure 600 includes openings 610 formed in the process layer 615, shown in cross-section in FIG. 6. In one embodiment, the process layer 615 is a poly-silicon layer. In one embodiment, during the fabrication of grating structure 600 on the semiconductor wafer 105, a layer of silicon nitride 630 is deposited on the semiconductor wafer 105 for use as a stop layer for chemical mechanical polishing. A layer of silicon dioxide 640 formed using tetraethoxysilane (TEOS) is formed over the silicon nitride 630 (i.e., other layers, such as a silicon oxinitride antireflective layer (not shown) and a liner oxide layer (not shown) may be disposed between the silicon nitride stop layer 630 and the silicon dioxide layer 640). The silicon nitride stop layer 630 is deposited over the entire semiconductor wafer 105, including over the grating structure 600. The silicon dioxide stop layer 640 is subsequently polished to remove excess material, and the silicon nitride stop layer 630 is stripped.

Figure 7A:
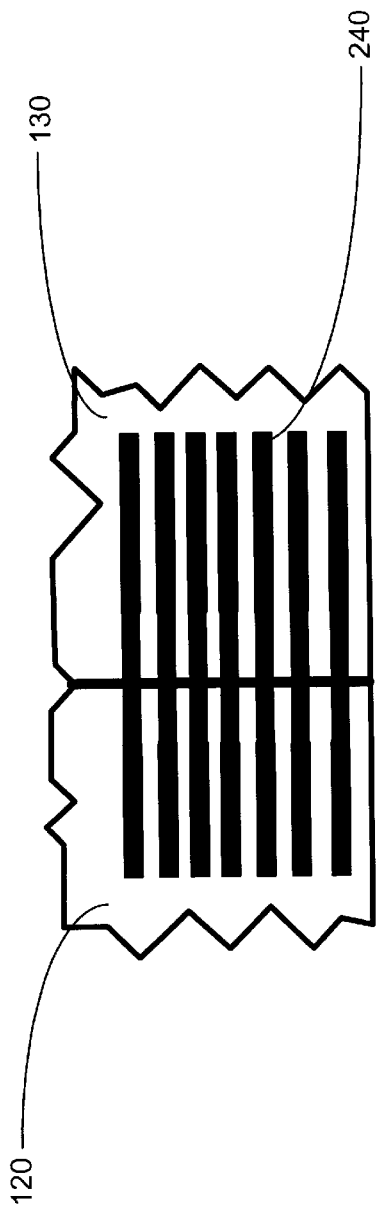
FIG. 7A illustrates a top view of a grating structure formed on the semiconductor wafer, in accordance with one embodiment of the present invention.
Figure 7B:
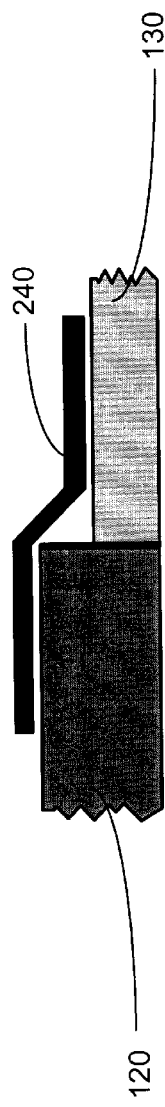
FIG. 7B illustrates a cross-sectional view of the grating structure formed on the semiconductor wafer, in accordance with one embodiment of the present invention.

In one embodiment, the grating structure 600 illustrated in FIG. 6 is formed such that a portion of the grating structure 600 is located in a field region 120 (shown in FIG. 7A) of the semiconductor wafer 105 being processed, and a portion of the grating structure 600 is located in an active region 130 (shown in FIG. 7A) of the semiconductor wafer 105. In one embodiment, the grating structure 600 can be within scribe lines. In an alternative embodiment, the grating structure 600 is a part of a process section. Turning now to FIG. 7, the grating structure 600 that overlaps a field region 120 and an active region 130 is shown. FIG. 7A shows a field region 120 and an active region 130 that are formed on the semiconductor wafer 105 being processed. In one embodiment the field region 120 may be made from field oxide material, such as silicon oxide. Generally, a field region 120 electrically isolates one active region 130 from another active region. The active regions 130 generally comprise transistors and other electrically active areas, such as the collector of a transistor. Line structures 155, such as poly-silicon lines are used to electrically connect one active region 130 with another. In an alternative embodiment, the methods of the present invention can be implemented upon grating structures 600 that are located entirely within a field region 120 or located entirely within an active region 130.

Once the grating structure 600, which in one embodiment overlaps the field region 120 and the active region 130, is in place, further error analysis can be performed. In one embodiment, a line structure fault detection process is performed by the system 300 (block 530). A flowchart depiction of the steps for performing the line structure fault detection process indicated in block 530 of FIG. 5, is shown in FIG. 8.

Figure 8:
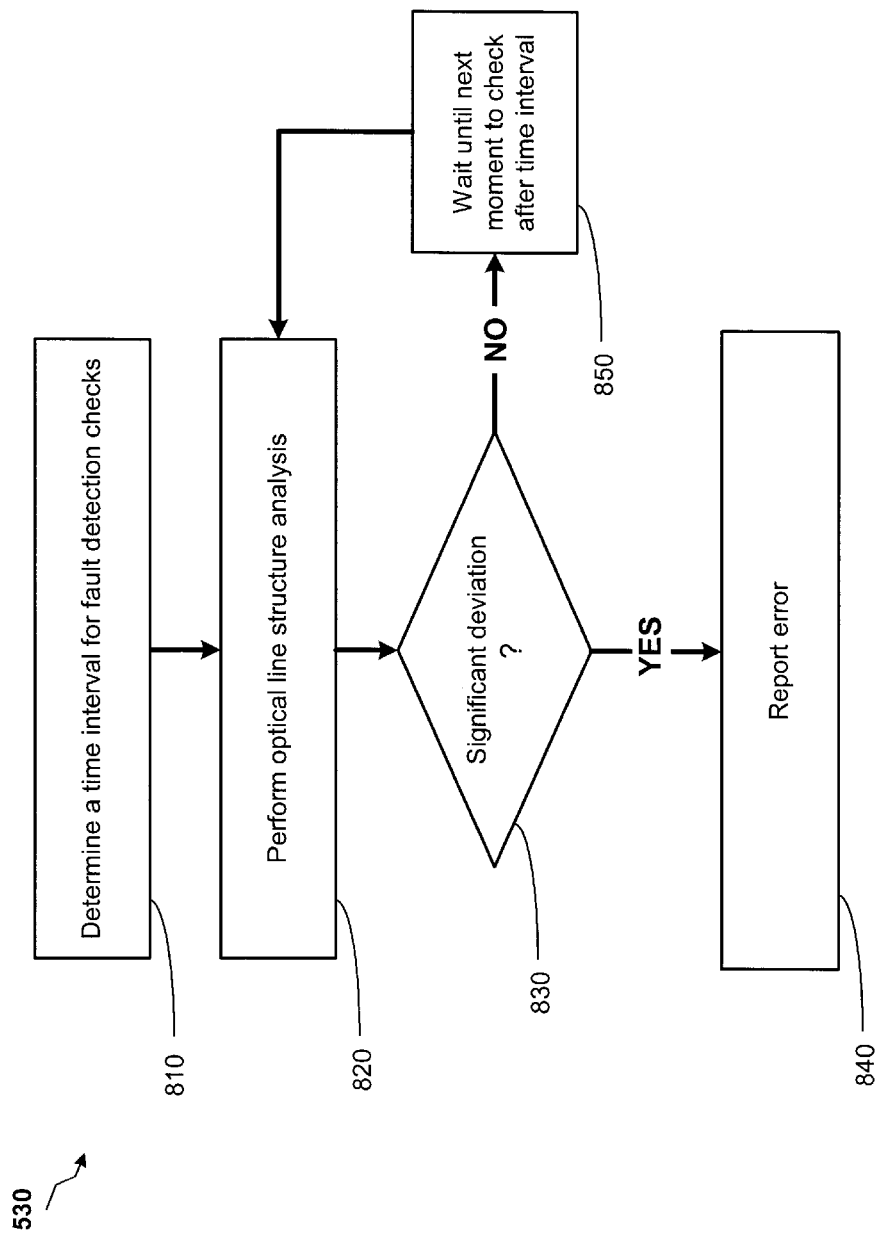
FIG. 8 illustrates a flowchart depiction of a method of performing a fault detection analysis described in FIG. 5, in accordance with one embodiment of the present invention.

Turning now to FIG. 8, a time interval in which to perform a fault detection analysis on semiconductor wafers 105 being processed, is determined by the system 300 (block 810). Generally, fault detection analyses are performed to detect significant, or gross, errors that occur during semiconductor processing. In order to reduce the possibility of gross errors occurring during manufacturing, semiconductor wafers 105 that are being processed are generally examined at a predetermined time interval. Those who are skilled in the art and have the benefit of the present disclosure can determine such a time interval. When a time interval for performing fault detection analysis is determined, at least one semiconductor wafer 105 is selected for optical line structure analysis (block 820). A more detailed description of the steps of performing the optical line structure analysis described in block 820 is provided below.

After performing an optical line structure analysis process, the system 300 determines whether a significant deviation from predetermined specifications has occurred in the semiconductor device that was examined (block 830). For example, the system 300 determines whether line-edge roughness is in an error condition. Those skilled in the art that have the benefit of the present disclosure can define the predetermined specifications. In one embodiment, a data comparison of the acquired metrology data and the data from the optical data reference library 365 is performed in order to determine whether there exists a significant deviation. When a determination is made that a significant deviation has occurred, the error is reported to the computer system 330. Operators of the system 300 can then be notified of the error report and make appropriate corrective measures, such as modifying control input parameters for subsequent processes and/or report the error (block 840). When a determination is made that there has been no significant deviation in the performance of the process, the system 300 waits during a time period prescribed by the predetermined time interval before performing a subsequent line structure fault detection check (block 850).

Figure 9:
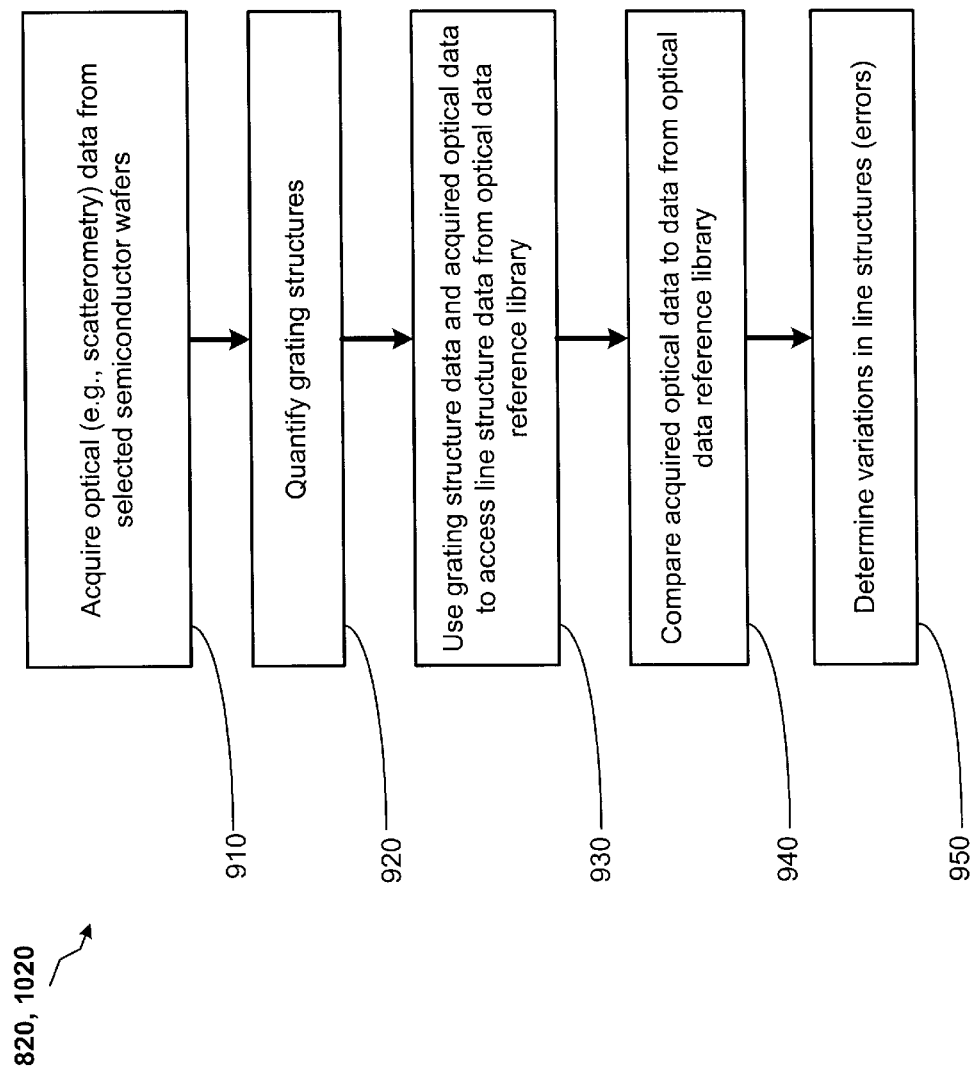
FIG. 9 illustrates a flowchart depiction of a method of performing an optical line structure analysis described in FIG. 8, in accordance with one embodiment of the present invention.

One embodiment of the step of performing the optical line formation analysis, depicted in a flow chart form, is illustrated in FIG. 9. Turning now to FIG. 9, optical data from selected semiconductor wafers 105 is acquired (block 910). In one embodiment, the optical data acquired is scatterometry data. In one embodiment, the scatterometry measurements are acquired such that the angles of incident of the incoming light are approximately parallel to the linear grating structure 600. Therefore, the goodness-of-fit (i.e., the measure of residual noise in the reflective measured light) can be used to quantify variations in the line structures 155, such as variations in the roughness of the line structures 155.

The system 300 quantifies the grating structures 600 (block 920). In one embodiment, the grating structures 600 are quantified by measuring film thicknesses, critical dimensions, profile data, and the like, relating to the lines in the grating structures 600. A number of methods may be used to acquire the film characteristics of the grating structures 600, such as scatterometry measurements. The system 300 uses the quantified grating structure data and the acquired optical data to access the line structure library data from the optical data reference library 365 (block 930). The quantification of the grating structures points to a particular location in the optical data reference library 365.

The optical data acquired from the semiconductor wafer 105 being examined is compared to the optical data (e.g., optical signatures) stored in the optical data reference library 365 (block 940). In one embodiment, the computer system 330 performs such a comparison. Since the grating structures 600 are quantified before data comparisons between the acquired line structure data and the library data are made, an assumption can be made that the primary cause of the variations (between the acquired metrology data and the modeled calculations) are generally due to line structure errors. Therefore, the system 300 is able to determine the amount of variations (or errors) in the line structures 155, such as the amount of line-edge roughness (block 950).

Turning back to FIG. 5, in addition to the line structure fault detection analysis described in block 530 of FIG. 5, the system 300 also performs a process control compensation procedure, as indicated in block 540 of FIG. 5. A flowchart depiction of one embodiment of the steps for performing the process control compensation described in block 540, is illustrated in FIG. 10.

Figure 10:
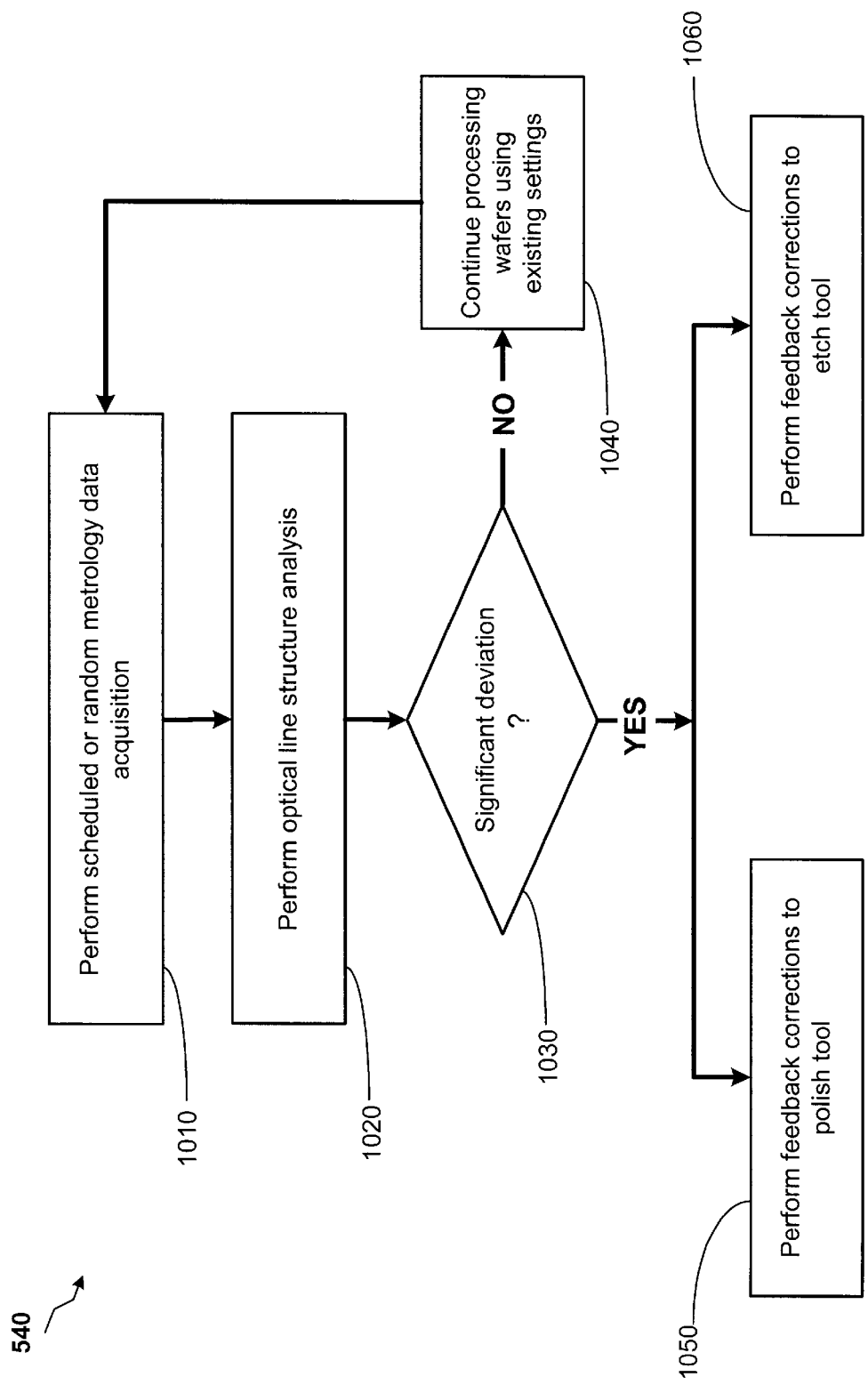
FIG. 10 illustrates a flowchart depiction of a method of performing a process control compensation process described in FIG. 5, in accordance with one embodiment of the present invention.

Turning now to FIG. 10, the system 300 performs a scheduled, or in an alternative embodiment, a random metrology data acquisition process, on semiconductor wafers 105 being processed (block 1010). In one embodiment, the metrology tool 350 acquires the metrology data. In one embodiment a scatterometry metrology device is used to acquire the metrology data. When the metrology data is acquired, an optical line structure analysis is performed using the acquired metrology data (block 1020). The scatterometry analysis indicated in block 1020 of FIG. 10 is substantially similar to the optical line structure analysis indicated in FIG. 9, which is described above.

Once the optical line structure analysis is performed, the system 300 makes a determination whether a significant deviation (i.e., a significant line structure error) has taken place (block 1030). When a determination is made that there is no significant deviation in comparison with a predetermined specification, the system 300 continues the processing of semiconductor wafers 105 using the existing settings (block 1040). When the system 300 determines that there is a significant deviation resulting from the optical line structure analysis, in one embodiment, the system 300 performs feedback corrections to a processing tool 310 that performs a polishing function (e.g., a polishing tool) (block 1050). The feedback corrections to the polishing tool can be used to reduce line structure errors.

In an alternative embodiment, feedback corrections can be made to a processing tool 310 that performs an etch function (block 1060). In one embodiment, in order to reduce the errors in the line structures 155, feedback control modifications to an etch tool can be used to prompt the etch tool to reduce the amount of line-edge roughness, particularly for dry-develop processes. The feedback corrections described above can be performed using the system 300 described in FIG. 3. Turning back to FIG. 5, once the line structure fault detection process, and/or the process control compensation process, are substantially complete, subsequent processing of semiconductor wafers 105 are performed based upon the results from the line characteristic fault detection process and the process control compensation process (block 550).

The principles taught by the present invention can be implemented in an Advanced Process Control (APC) Framework. The APC is a preferred platform from which to implement the control strategy taught by the present invention. In some embodiments, the APC can be a factory-wide software system, therefore, the control strategies taught by the present invention can be applied to virtually any of the semiconductor manufacturing tools on the factory floor. The APC framework also allows for remote access and monitoring of the process performance. Furthermore, by utilizing the APC framework, data storage can be more convenient, more flexible, and less expensive than local drives. The APC platform allows for more sophisticated types of control because it provides a significant amount of flexibility in writing the necessary software code.

Deployment of the control strategy taught by the present invention onto the APC framework could require a number of software components. In addition to components within the APC framework, a computer script is written for each of the semiconductor manufacturing tools involved in the control system. When a semiconductor manufacturing tool in the control system is started in the semiconductor manufacturing fab, it generally calls upon a script to initiate the action that is required by the process controller, such as the overlay controller. The control methods are generally defined and performed in these scripts. The development of these scripts can comprise a significant portion of the development of a control system. The principles taught by the present invention can be implemented into other types of manufacturing frameworks.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method, comprising:
   processing at least one semiconductor wafer;
   acquiring metrology data from said processed semiconductor wafer;
   acquiring film property data from said semiconductor wafer;
   accessing data from a reference library comprising optical data relating to a line structure formation on a semiconductor wafer, based upon said film property data, said line structure being formed on at least a portion of an active region and on at least a portion of a field region of said semiconductor wafer;
   comparing said metrology data to data from said reference library; and
   performing a line structure fault detection analysis in response to said comparison of said metrology data and said reference library data, said line structure fault detection analysis comprises checking for a error relating to said line structure in an area proximate to a transition between said active and field regions.

2. The method described in claim 1, further comprising generating said reference library that comprises optical data relating to characteristics of a plurality of line structures.

3. The method described in claim 1, wherein processing at least one semiconductor wafer comprises performing a photolithography process on said semiconductor wafer.

4. The method described in claim 3, wherein processing at least one semiconductor wafer further comprises performing an etch process on said semiconductor wafer.

5. The method described in claim 3, wherein processing at least one semiconductor wafer further comprises performing a chemical-mechanical polishing (CMP) process on said semiconductor wafer.

6. The method described in claim 1, wherein processing at least one semiconductor wafer comprises forming a grating structure.

7. The method described in claim 6, wherein acquiring metrology data from said processed semiconductor wafer comprises:
   illuminating at least a portion of said grating structure; and
   measuring reflected light resulting from said illumination to generate an optical signature of said grating structure.

8. The method described in claim 7, wherein acquiring metrology data from said processed semiconductor wafer further comprises performing scatterometry data acquisition.

9. The method described in claim 8, wherein performing a line structure fault detection analysis in response to said comparison of said metrology data and said reference library data further comprises:
   quantifying grating structures based upon said film property data;
   using grating structure data and said acquired optical data to access stored line structure reference data; and
   determining at least one variation in a line structure based upon a comparison of said acquired optical data and said reference data.

10. The method described in claim 9, further comprising performing a process control compensation in response to said comparison of said metrology data and said reference library data.

11. The method described in claim 10, wherein comprising performing a process control compensation in response to said comparison of said metrology data and said reference library data further comprises modifying at least one control parameter capable of controlling at least one step relating to processing a subsequent semiconductor wafer, in response to said comparison of said metrology data and said reference library data.

12. A method, comprising:
   processing at least one semiconductor wafer;
   generating a reference library, said reference library comprising a plurality of optical data relating to a plurality of line structures formed on said semiconductor wafer;
   illuminating at least a portion of said semiconductor wafer;
   measuring reflected light off said line structures to generate an optical signature of said line structures, said line structure being formed on at least a portion of an active region and on at least a portion of a field region of said semiconductor wafer;
   comparing said measured reflected light related to said line structure with optical data from said reference library based upon constant film property values;
   performing at least one of a line structure fault detection analysis and a process control compensation in response to said comparison of said measured reflected light and said optical data from said reference library, said line structure fault detection analysis comprises checking for a error relating to said line structure in an area proximate to a transition between said active and field regions.

13. The method described in claim 12, wherein illuminating at least a portion of said semiconductor wafer further comprises illuminating a line structure on said semiconductor wafer.

14. The method described in claim 12, wherein measuring reflected light resulting from said illumination to generate an optical signature of said line structure comprises performing scatterometry data acquisition.

15. The method described in claim 12, wherein performing said line structure fault detection analysis in response to said comparison of said measured reflected light and said optical data from said reference library further comprises:
    quantifying grating structures based upon said film property data;
    using grating structure data and said acquired optical data to access stored line structure reference data; and
    determining at least one variation in a line structure based upon a comparison of said acquired optical data and said reference data.

16. The method described in claim 12, wherein performing a process control compensation in response to said comparison of said measured reflected light and said optical data from said reference library comprises modifying at least one control parameter capable of controlling at least one step relating to processing a subsequent semiconductor wafer, in response to a said comparison of said measured reflected light and said reference library data.

17. A system, comprising:
    a computer system;
    a manufacturing model coupled with said computer system, said manufacturing model being capable of generating and modifying at least one control input parameter signal capable of controlling at least one step relating to processing a semiconductor wafer;
    a machine interface coupled with said manufacturing model, said machine interface being capable of receiving process recipes from said manufacturing model;
    a processing tool capable of processing semiconductor wafers and coupled with said machine interface, said first processing tool being capable of receiving at least one control input parameter signal from said machine interface;
    a metrology tool coupled with said first processing tool and said second processing tool, said metrology tool being capable of acquiring metrology data;
    an optical data reference library, said optical data reference library comprising optical data related to a plurality of line structures, said line structure being formed on at least a portion of an active region and on at least a portion of a field region of said semiconductor wafer; and
    an optical data error analysis unit coupled to said metrology tool and said optical data reference library, said scatterometry data error analysis unit capable of comparing said metrology data to corresponding data in said optical data reference library and calculating at least one of a line-edge error and a line structure in response to said comparison.

18. The system of claim 17, wherein said computer system is capable of generating modification data for modifying at least one said control input parameter in response to said calculation of at least one line-edge error.

19. The system of claim 18, wherein said manufacturing model is capable of modifying said control input parameter in response to said modification data.

20. The system of claim 17, wherein said metrology tool is a scatterometer.

21. An apparatus, comprising:
    means for processing at least one semiconductor wafer;
    means for acquiring metrology data from said processed semiconductor wafer;
    means for acquiring film property data from said semiconductor wafer;
    means for accessing data from a reference library comprising optical data relating to a line structure formation on a semiconductor wafer, based upon said film property data, said line structure being formed on at least a portion of an active region and on at least a portion of a field region of said semiconductor wafer;
    means for comparing said metrology data to data from said reference library; and
    means for performing a line structure fault detection analysis in response to said comparison of said metrology data and said reference library data, said means for performing said line structure fault detection analysis comprises means for checking for a error relating to said line structure in an area proximate to a transition between said active and field regions.

22. A computer readable program storage device encoded with instructions that, when executed by a computer, performs a method, comprising:
    processing at least one semiconductor wafer;
    acquiring metrology data from said processed semiconductor wafer;
    acquiring film property data from said semiconductor wafer;
    accessing data from a reference library comprising optical data relating to a line structure formation on a semiconductor wafer, based upon said film property data, said line structure being formed on at least a portion of an active region and on at least a portion of a field region of said semiconductor wafer;
    comparing said metrology data to data from said reference library; and
    performing a line structure fault detection analysis in response to said comparison of said metrology data and said reference library data, said line structure fault detection analysis comprises checking for a error relating to said line structure in an area proximate to a transition between said active and field regions.

23. The computer readable program storage device encoded with instructions that, when executed by a computer, performs the method described in claim 22, further comprising generating said reference library that comprises optical data relating to characteristics of a plurality of line structures.

24. The computer readable program storage device encoded with instructions that, when executed by a computer, performs the method described in claim 22, wherein processing at least one semiconductor wafer comprises performing a photolithography process on said semiconductor wafer.

25. The computer readable program storage device encoded with instructions that, when executed by a computer, performs the method described in claim 22, wherein processing at least one semiconductor wafer further comprises performing an etch process on said semiconductor wafer.

26. The computer readable program storage device encoded with instructions that, when executed by a computer, performs the method described in claim 22, wherein processing at least one semiconductor wafer further comprises performing chemical-mechanical polishing (CMP) process on said semiconductor wafer.

27. The computer readable program storage device encoded with instructions that, when executed by a computer, performs the method described in claim 22, wherein processing at least one semiconductor wafer comprises forming a grating structure.

28. The computer readable program storage device encoded with instructions that, when executed by a computer, performs the method described in claim 27, wherein acquiring metrology data from said processed semiconductor wafer comprises:

illuminating at least a portion of said grating structure; and measuring reflected light resulting from said illumination to generate an optical signature of said grating structure.

29. The computer readable program storage device encoded with instructions that, when executed by a computer, performs the method described in claim 27, wherein acquiring metrology data from said processed semiconductor wafer further comprises performing scatterometry data acquisition.

30. The computer readable program storage device encoded with instructions that, when executed by a computer, performs the method described in claim 29, wherein performing a line structure fault detection analysis in response to said comparison of said metrology data and said reference library data further comprises:

quantifying grating structures based upon said film property data;

using grating structure data and said acquired optical data to access stored line structure reference data; and determining at least one variation in a line structure based upon a comparison of said acquired optical data and said reference data.

31. The computer readable program storage device encoded with instructions that, when executed by a computer, performs the method described in claim 30, further comprising performing a process control compensation in response to said comparison of said metrology data and said reference library data.

32. The computer readable program storage device encoded with instructions that, when executed by a computer, performs the method described in claim 31, wherein comprising performing a process control compensation in response to said comparison of said metrology data and said reference library data further comprises modifying at least one control parameter capable of controlling at least one step relating to processing said semiconductor wafer, in response to said comparison of said metrology data and said reference library data.

33. The method described in claim 1, wherein performing a line structure fault detection analysis in response to said comparison of said metrology data and said reference library data further comprises determining an amount of necking relating to said line structures in said area proximate to said transition between said field and active regions.

34. The computer readable program storage device encoded with instructions that, when executed by a computer, performs the method described in claim 22, wherein performing a line structure fault detection analysis in response to said comparison of said metrology data and said reference library data further comprises determining an amount of necking relating to said line structures in said area proximate to said transition between said field and active regions.

* * * * *

UNITED STATES PATENT AND TRADEMARK OFFICE
CERTIFICATE OF CORRECTION

PATENT NO. : 6,697,153 B1  Page 1 of 1
DATED : February 24, 2004
INVENTOR(S) : Marilyn I. Wright and James B. Stirton It is certified that error appears in the above-identified patent and that said Letters Patent is hereby corrected as shown below:

Column 2,
Line 31, replace "very." with -- very --.

Signed and Sealed this

Twenty-ninth Day of June, 2004

JON W. DUDAS
*Acting Director of the United States Patent and Trademark Office*